(12) United States Patent
Park et al.

(10) Patent No.: US 6,403,111 B1
(45) Date of Patent: Jun. 11, 2002

(54) METHOD FOR PREPARING AQUEOUS PHYTOSPHINGOSINE SOLUTION

(75) Inventors: Chang Seo Park, Kwachon; Jin Wook Kim, Yongin; Jee Hean Jeong, Suwon, all of (KR)

(73) Assignee: Doosan Corporation, Seoul (KR)

( * ) Notice: Subject to any disclaimer, the term of this patent is extended or adjusted under 35 U.S.C. 154(b) by 0 days.

(21) Appl. No.: 09/691,469

(22) Filed: Oct. 18, 2000

(51) Int. Cl.$^7$ .......................... A61K 35/78; A61K 7/00
(52) U.S. Cl. ...................... 424/401; 424/769; 424/755; 514/844
(58) Field of Search ................................ 424/401, 769, 424/775; 514/844

(56) References Cited

U.S. PATENT DOCUMENTS 5,368,857 A * 11/1994 Corcoran et al.
5,882,665 A * 3/1999 Meyers et al.

\* cited by examiner

Primary Examiner—Francisco Prats
Assistant Examiner—Susan D. Coe
(74) Attorney, Agent, or Firm—Ladas & Parry

(57) ABSTRACT

Disclosed is a method for preparing an aqueous phytosphingosine solution containing as much as 5–10 weight % of phytosphingosine without using any solvents other than water. A high content of phytosphingosine is dissolved in water and lactic acid with the help of a willow bark extract. In addition to being clear, the aqueous phytosphingosine solution is able to recover damaged skin with activity against bacteria and inflammation. Also, when being applied for cosmetics, the aqueous phytosphingosine solution allows them to contain as much as 1–2 weight % of phytosphingosine by virtue of its high content of phytosphingosine. Further, the phytosphingosine solution is greatly improved in compatibility with cosmetic components so that it can be readily applied for aqueous cosmetics such as skin lotions, essence lotions, aqueous pack products, body essence compositions, etc., for which phytosphingosine has not yet been applied, thus far. Thus, the phytosphingosine solution of the present invention gives a great contribution to the functional improvement of aqueous cosmetics.

5 Claims, No Drawings

METHOD FOR PREPARING AQUEOUS PHYTOSPHINGOSINE SOLUTION

BACKGROUND OF THE INVENTION

1. Field of the Invention

The present invention relates to a method for preparing a clear, aqueous solution containing as much as 5–10% of phytosphingosine by use of water, and using no alcohols or other organic solvents.

More particularly, the present invention relates to a method for preparing an aqueous phytosphingosine solution by heating a solution of 5–10 weight % of a phytosphingosine powder in distilled water at 60–90° C. with stirring, solubilizing the phytosphingosine with the pH being neutralized with lactic acid, and adding 0.1–1 wt % of a willow bark extract containing 10 weight % or more of salicylic acid or its analogues such as salicylin to give a clear phase of the aqueous phytosphingosine solution.

2. Description of the Prior Art

Phytosphingosine, a kind of sphingolipid serving as an important component of cell membranes, is a physiologically active material with a variety of biological functions, including being an important structural constituent of cell membranes and an important signal transmitter in a signal transduction system (Okasaki et al., 1989; Kim et al., 1991).

Recent research has revealed that sphingolipids play a critical role in cellular functions, including the growth, proliferation, differentiation and apoptosis of cells, through a signal transduction process known as the "sphinogmyelin cycle" (Hannun, 1994, 1996; Hannun and Obeid, 1995) in which many other factors such as TNF-α, IL-1, γ-IFN and FAS ligands are involved.

Sphingolipids are responsible for maintaining moisture balance of skin and regenerating stratum corneum as well as functioning as a primary defense against external attack from microbes. In addition, sphingolipids are now used in cancer research, as they are known to be involved in the inactivation and activation of protein kinase C, the regulation of EGF receptors, the induction of $Ca^{2+}$ ion mobilization, and the regulation of the NF-κB gene expression. Disclosing that most skin diseases, including atopic dermatitis, from which over 3–4% of the world population is suffering, are at least partially attributed to a decrease in the content of various sphingolipids in the stratum corneum, recent research reports strongly suggest that the use of sphingolipids is highly feasible as active ingredients of next generation curing agents for skin diseases, substituting for antibiotics and steroid hormones which serve as anti-inflammatory agents.

Ceramides III and VI, which have phytosphingosine as their sphingolipid long-chain base, have been used as important cosmeceuticals in a broad spectrum of cosmetic and pharmaceutical industries for recent years. For instance, ceramides (e.g., N-acylated sphingosine and N-acylated phytosphingosine), which constitute higher than 40 weight % of the total lipids in stratum corneum, are being used worldwide in various products from cosmetic compositions for skin care to hair tonics. Phytosphingosine itself is used as a functional material for moisturizing compositions and anti-aging compositions in the cosmetic industry. The applications of phytosphingosine are sharply increasing because it is better in skin recovery properties and anti-bacterial and anti-inflammatory activity than are ceramides. In the pharmaceutical industry, for example, the use of phytosphingosine in the treatment of atopic dermatitis, acne, psoriasis, itching and wound recovery is under study. Therefore, it is expected that phytosphingosine would be used as a core material of functional cosmeceuticals applicable in, for example, anti-aging agents, moisturizing agents, damaged skin-recovery agents, and applicable for the healing of, for example, atopic dermatitis, acne, psoriasis and itching, and wounds.

Until recently, sphingolipids had usually been obtained from animals. However, the cosmetic industry is reluctant to use sphingolipids from animals for fear of contamination with Mad Cow Disease. Their chemical synthesis suffers from many disadvantages. For example, the chemical synthesis is prohibitively expensive. Further, in many cases, the stereochemical structures of the compounds synthesized are different from those of the sphingolipids occurring naturally in the body. It is also difficult to chemically synthesize pure stereochemical structures of sphingolipids. In recent, there have been developed processes for preparing phytosphingosine through the fermentation of the yeast Pichia cifferi. Since the phytosphingosine prepared from the yeast fermentation was also found to be stereo-chemically the same as that existing in the human body, it is being used in many industries in sharply increasing quantities. The phytosphingosine which can be prepared from the yeast fermentation, however, finds difficulty in its application to cosmetics and pharmaceuticals owing to its low solubility. Phytosphingosine is not soluble in water at all and shows a solubility of 1 wt % even in isocetyl alcohol, a widely used cosmetic solvent. Thus, phytosphingosine is difficult to use at an amount large enough to exert its efficacy when being used as a cosmetic material. Moreover, it cannot be used in a transparent liquid product, such as a skin lotion, at all.

At present, phytosphingosine is being used at an amount of 0.1–0.3 weight % in cosmetic products, but these concentrations are too low to obtain desired effects. The expression of functions of phytosphingosine requires at least 0.5 weight % and preferably 1–2 weight % of the active compound in cosmetic products. Therefore, there remains a need for developing a process of solubilizing phytosphingosine at a higher concentration in order for phytosphingosine to be applied for use in cosmetics and pharmaceuticals.

SUMMARY OF THE INVENTION

Leading to the present invention, the intensive and thorough research on the effective application of phytosphingosine for use in cosmetics and pharmaceuticals, repeated by the present inventors aiming to solve the above problems encountered in prior arts, resulted in the finding that a mixture of water and lactic acid can solubilize a large quantity of phytosphingosine with the aid of a willow bark extract, and no recrystallization occurs in the resulting phytosphingosine solution.

Therefore, it is an object of the present invention to provide a method for preparing a clear aqueous solution with a high content of phytosphingosine.

It is another object of the present invention to provide use of the aqueous phytosphingosine solution in cosmetics.

In accordance with the present invention, there is provided a method for preparing an aqueous phytosphingosine solution, comprising the steps of: heating a solution of a predetermined concentration of a Phytosphingosine powder in distilled water at 60–90° C. with stirring; neutralizing, in pH, the solution with lactic acid to solubilize the Phytosphingosine with stirring; and adding a willow bark extract to prevent the recrystallization of the solution.

The aqueous phytosphingosine solution prepared according to the present invention is able to care troubled skin with inhibitory activity against bacteria and inflammation. In addition, when being applied for cosmetics, the aqueous phytosphingosine solution allows them to contain as much as 1–2 weight % of phytosphingosine by virtue of its high content of phytosphingosine. Thus, the present Phytosphingosine solution provides a significant improvement in applications over conventional solutions that require additional dissolution of phytosphingosine in solvents. Further, the phytosphingosine solution of the present invention is greatly improved in compatibility with cosmetic components so that it can be readily applied for aqueous cosmetics such as skin lotions, essence lotions, aqueous pack products, body essence compositions, etc., for which phytosphingosine has not yet been applied thus far.

Accordingly, the phytosphingosine solution of the present invention gives a great contribution to the functional improvement of aqueous cosmetics. An aqueous phase of phytosphingosine is applied for conventional cosmetic cream products, including skin care compositions, with greater ease than is a powder phase.

DETAILED DESCRIPTION OF THE INVENTION

The present invention is directed to the solubilization of a high amount of phytospingosine in an aqueous solvent. Instead of isocetyl alcohol, a mixture of water, lactic acid and a willow bark extract is used as the aqueous solvent, in accordance with the present invention. As much as 5–10 weight % of phytosphingosine can be solubilized in the solvent to give a completely clear solution.

In more detail, phytosphingosine powder is added at an amount of 0.1–10 weight % and preferably at an amount of 0.5–6 weight % in distilled water and heated to about 80° C. for 30–40 min with stirring. Subsequently, lactic acid is dropwise added to neutralize, in pH, the solution that is heated at an elevated temperature while being stirred to the complete solubilization of phytosphingosine. Preferably, lactic acid is used at an amount of 0.2–4 g per g of phytosphingosine. The phytosphingosine powder may be a commercially available one, such as that sold by Doosan, Korea, under the brand name of DS-Phytosphingosine.

A preferable solubilizing temperature of phytosphingosine falls within the range of 60–90° C. Depending on the concentration of the phytosphingosine added, the stirring is preferably conducted for a period of 30–50 min. After completion of the solubilization of phytosphingosine, a willow bark extract with a 10 % content of salicylic acid and salicylin, commercially available from Brook Co. Ltd., U.S.A., is slowly added at an amount of 0.1–10 weight % to the solution with stirring, so as to give an aqueous clear solution with a high content of phytosphingosine.

Where phytosphingosine is dissolved only in acid such as lactic acid, recrystallization occurs at low temperatures or with the passage of time. In contrast, where phytosphingosine is dissolved in a mixture of lactic acid and a willow bark extract, the resulting solution can be maintained in an aqueous state or a clear gel state without occurrence of any changes even at low temperatures or even with the lapse of a long period of time.

To obtain a clear phase of an aqueous, concentrated phytosphingosine solution, the willow bark extract is preferably added in the range of 0.1–10 weight % for 0.5–3 weight % phytosphingosine solutions and in the range of 2–10 weight % for 5–10 weight % phytosphingosine solutions. For example, if the willow bark extract is added at an amount less than the lower limits, the phytosphingosine solution is recrystallized. On the other hand, when the willow bark extract is used at an amount greater than 10 weight %, the phytosphingosine solution becomes too viscous to be compatible with other cosmetic components. Application of such viscous phytosphingosine solutions for cosmetic products such as creams, skin lotions, aqueous packs, etc., requires their re-dissolution.

A better understanding of the present invention may be obtained in light of the following examples which are set forth to illustrate, but are not to be construed to limit the present invention.

EXAMPLE 1

Preparation of Aqueous Phytosphingosine Solution

A 0.1 weight % solution of phytosphingosine powder in 100 ml of distilled water was slowly heated to about 82° C. with stirring at 70 rpm. During the stirring, 0.2 g of lactic acid was added to neutralize, in pH, the solution to solubilize phytosphingosine. After 30 min of stirring, it was confirmed with the eye whether the phytospingosine was thoroughly dissolved. Under the same stirring condition, a willow bark extract was dropwise added at an amount of 2 weight % to give an aqueous phytosphingosine solution which was slightly opaque and viscous.

EXAMPLE 2

Preparation of Aqueous Phytosphingosine Solution

A 5 weight % solution of phytosphingosine powder in 100 ml of distilled water was slowly heated to about 82° C. with stirring at 80 rpm. During the stirring, 0.5 g of lactic acid was added to neutralize, in pH, the solution to solubilize phytosphingosine. After 30 min of stirring, it was confirmed with the eye whether the phytospingosine was thoroughly dissolved. Under the same stirring condition, a willow bark extract was dropwise added at an amount of 1 weight % to give a clear aqueous phytosphingosine solution.

EXAMPLE 3

Preparation of Aqueous Phytosphingosine Solution

A 5 weight % solution of phytosphingosine powder in 100 ml of distilled water was slowly heated to about 80° C. with stirring at 95 rpm. During the stirring, 6 g of lactic acid was added to neutralize, in pH, the solution to solubilize phytosphingosine. After 35 min of stirring, it was confirmed with the eye whether the phytospingosine was thoroughly dissolved. Under the same stirring condition, a willow bark extract was dropwise added at an amount of 2 weight % to give a clear aqueous phytosphingosine solution.

TEST EXAMPLE 1

Change in Viscosity of Aqueous Phytosphingosine Solution

In eight 300 ml four-neck flasks, each containing 100 ml of distilled water, phytosphingosine was added at amounts of 0.1, 0.5, 1, 3, 5, 6, 8 and 10 weight %, respectively. The solutions were heated at about 80° C. and added with 0.2–0.5 g of lactic acid per g of phytosphingosine with stirring. After confirming the thorough solubilization of the phytosphingosine with the naked eye, a willow bark extract was added at amounts of 0.1, 0.5, 1, 2, 3, 4, 5, and 10 weight %, respectively, to the flasks. After sufficient stirring, the resulting aqueous phytosphingosine solutions were measured for viscosities. The results are given in Table 1, below.

As seen in Table 1, the aqueous phytosphingosine solution becomes highly viscous as the concentration of phytosphingosine and/or the willow bark extract increases. The most stable aqueous phase of the phytosphingosine solution was obtained at a phytosphingosine content of 3–6 weight % in the range of 0.1–3 weight % of the willow bark extract.

TABLE 1

Change in the Viscosity of Phytosphingosine Solutions According to Concentrations of Willow Bark Extract

| Conc. Of Phytosphingosine | Conc. Of Willow Bark Extract | | | | | | | |
|---|---|---|---|---|---|---|---|---|
| | 0.1% | 0.5% | 1% | 2% | 3% | 4% | 5% | 10% |
| 10% | 1 | 1 | 1 | 2 | 4 | 5 | 5 | 5 |
| 8% | 1 | 1 | 1 | 1 | 3 | 4 | 5 | 5 |
| 6% | 1 | 1 | 1 | 1 | 2 | 4 | 5 | 5 |
| 5% | 1 | 1 | 1 | 1 | 1 | 4 | 5 | 5 |
| 3% | 1 | 1 | 1 | 1 | 2 | 4 | 5 | 5 |
| 1% | 1 | 1 | 1 | 3 | 4 | 4 | 4 | 4 |
| 05% | 1 | 1 | 1 | 4 | 4 | 4 | 4 | 4 |
| 0.1% | 1 | 2 | 2 | 3 | 3 | 4 | 4 | 4 |

1–2: not viscous, 3–4: slightly viscous, 5: highly viscous (gel)

TEST EXAMPLE 2

Clearness of Aqueous Phytosphingosine Solution

As in Test Example 1, phytosphingosine was added at amounts of 0.1, 0.5, 1, 3, 5, 6, 8 and 10 weight %, respectively. The solutions were heated at about 80° C. and added with 0.2~0.5 g of lactic acid per g of phytosphingosine with stirring. After confirming the thorough solubilization of the phytosphingosine with the naked eye, a willow bark extract was added at amounts of 0.1, 0.5, 1, 2, 3, 4, 5, and 10 weight %, respectively, to the flasks. After sufficient stirring, the resulting aqueous phytosphingosine solutions were examined for clearness. The results are given in Table 2, below.

As indicated in Table 2, when the willow bark extract is added at an amount of 1 weight % or less in 6 weight % or higher phytosphingosine solutions, recrystallization occurs. Also, 5 weight % phytosphingosine solutions recrystallize in the presence of as low as 0.5 weight % of the willow bark extract. On the other hand, the phytosphingosine solutions remain clear when the willow bark extract is added at an amount of 0.1–3 weight % in the presence of 0.5–3 weight % of phytosphingosine and at an amount of 2–10 weight % in the presence of 2–10 weight % of phytosphingosine.

TABLE 2

Change in the Transparency of Phytosphingosine Solutions According to Concentrations of Willow Bark Extract

| Conc. Of Phytosphingosine | Conc. Of Willow Bark Extract | | | | | | | |
|---|---|---|---|---|---|---|---|---|
| | 0.1% | 0.5% | 1% | 2% | 3% | 4% | 5% | 10% |
| 10% | Recry. | Recry. | Recry. | 1 | 1 | 1 | 1 | 1 |
| 8% | Recry. | Recry. | Recry. | 1 | 1 | 1 | 1 | 1 |
| 6% | Recry. | Recry. | Recry. | 1 | 1 | 1 | 1 | 1 |
| 5% | Recry. | Recry. | 1 | 1 | 1 | 1 | 1 | 1 |
| 3% | 1 | 1 | 1 | 1 | 1 | 1 | 1 | 1 |
| 1% | 1 | 1 | 1 | 1 | 1 | 1 | 1 | 1 |
| 05% | 1 | 1 | 1 | 1 | 1 | 1 | 1 | 1 |
| 0.1% | 3 | 3 | 3 | 4 | 4 | 5 | 4 | 3 |

1: clear, 3: slightly opaque, 5: opaque

TEST EXAMPLE 3

Anti-Bacterial Activity of Aqueous Phytosphingosine Solution

In a four-neck flask containing 100 ml of distilled water was added 5 weight % of phytosphingosine which was then heated at about 80° C. with stirring. 2.8 g of lactic acid was dropwise added with stirring to solubilize the phytosphingosine. After confirmation of the thorough solubilization of the phytosphingosine with the naked eye, a willow bark extract was added at an amount of 1 weight % to give a clear aqueous phytosphingosine.

In order to determine the anti-bacterial activity of the aqueous 5 weight % phytosphingosine solution (with 1 weight % of a willow bark extract), an examination was made of its inhibitory activity against the growth of microbes which causes skin troubles, such as *Staphylococcus aureus*, and *Propionibacterium acnes*. These test strains were diluted in a buffer to a cell density of 3,000–4,000 cells/ml. After being added with phytosphingosine at amounts of 100, 10, 1 and 0.1 µg/ml, the cell dilutions were allowed to stand at 37° C. for 1 hour and then, spread over agar plates. After 24 hours of incubation, appearing colonies were counted. For comparison, an aqueous 5 weight % phytosphingosine solution added with no willow bark extract, a solution of phytosphingosine in alcohol, and the willow bark extract itself were used as controls.

The results are given in Tables 3 and 4, below.

TABLE 3

Anti-Bacterial Activity of Phytosphingosine Against *Staphylococcus aureus*

| | Conc. of Phytosphingosine | | | Unit: no. of colonies |
|---|---|---|---|---|
| | 1 µg/ml | 0.5 µg/ml | 0.1 µg/ml | None |
| Control 1 | 6 | 271 | 1,267 | 1,520 |
| Control 2 | 36 | 449 | 1,084 | 1,520 |
| Control 3 | 1,056 | 1,465 | 1,516 | 1,520 |
| The present | 0 | 155 | 1,366 | 1,520 |

Note: control 1: 5 wt % phytosphingosine solution in cetyl alcohol
Control 2: 5 wt % phytosphingosine solution in lactic acid lacking willow bark extract
Control 3: willow bark extract

TABLE 4

Anti-Bacterial Activity of Phytosphingosine Against *Propionibacterium acnes*

| | Conc. of Phytosphingosine | | | Unit: no. of colonies |
|---|---|---|---|---|
| | 1 µg/ml | 0.5 µg/ml | 0.1 µg/ml | None |
| Control 1 | 3 | 125 | 938 | 1,726 |
| Control 2 | 24 | 217 | 1,058 | 1,726 |
| Control 3 | 1,358 | 1,537 | 1,648 | 1,726 |
| The present | 0 | 78 | 857 | 1,726 |

Note: control 1: 5 wt % phytosphingosine solution in cetyl alcohol
Control 2: 5 wt % phytosphingosine solution in lactic acid lacking a willow bark extract
Control 3: willow bark extract As apparent from Tables 3 and 4, the aqueous phytosphingosine solutions according to the present invention are superior to conventional phytosphingosine solutions in anti-bacterial activity against *Staphylococcus aureus* and *Propionibacterium acnes*.

TEST EXAMPLE 4

Inhibitory Activity of Cosmetic Phytosphingosine Cream Composition Against Microbes Inhabiting Skin In order to determine whether the anti-bacterial activity of phytosphingosine is effective when the aqueous phytosphingosine solutions of the present invention are applied for cosmetics, a cosmetic cream composition containing the aqueous 5 wt % phytosphingosine solution prepared in Test Example 3 was applied only to one side of the face of each of nine testees and a measurement was made of the change in the population of the microbes which inhabited the skin. The cosmetic cream composition was prepared by completely dissolving 2.5 g of cholesterol, 1.5 g of stearic acid, 3.5 g of ceramide, 1.5 g of oleic acid and 1.5 g of hydrated lecithin in 2.5 g of glyceride and adding 100 ml of the aqueous 5 wt % phytosphingosine solution. 2 hours after the application of the cream composition to one side, an examination was made of the distribution of microbes on both sides of the face. The results are given in Table 5, below.

TABLE 5

Inhibitory Effect of Cosmetic Phytosphingosine Cream Composition Against Epidermal Microbes Unit: no. of colonies

| Test Subject No. | Applied Side | Non-Applied Side | % Reduction |
| --- | --- | --- | --- |
| 1 | 126 | 1,328 | 90% |
| 2 | 268 | 584 | 54% |
| 3 | 189 | 249 | 24% |
| 4 | 520 | 2,056 | 75% |
| 5 | 208 | 2,136 | 90% |
| 6 | 110 | 1,056 | 90% |
| 7 | 372 | 3,680 | 90% |
| 8 | 386 | 580 | 33% |
| 9 | 320 | 3,891 | 92% |

It is apparent from Table 5 that the aqueous phytosphingosine solution of the present invention has a significant inhibitory effect against epidermal microbes.

As described hereinbefore, the aqueous phytosphingosine solution prepared according to the present invention is able to recover damaged skin with activity against bacteria and inflammation. In addition, when being applied for cosmetics, the aqueous phytosphingosine solution allows them to contain as much as 1–2 weight % of phytosphingosine by virtue of its high content of phytosphingosine. Thus, the phytosphingosine solution brings about a greater improvement in the convenience of use than do conventional solutions that require additional dissolution of phytosphingosine in solvents. Further, the phytosphingosine solution of the present invention is greatly improved in compatibility with cosmetic components so that it can be readily applied for aqueous cosmetics such as skin lotions, essence lotions, aqueous pack products, body essence compositions, etc., for which phytosphingosine has not yet been applied thus far. Accordingly, the phytosphingosine solution of the present invention gives a great contribution to the functional improvement of aqueous cosmetics. An aqueous phase of phytosphingosine is applied for conventional cosmetic cream products, including skin care compositions, with greater ease than is a powder phase.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A method for preparing an aqueous phytosphingosine solution, comprising the steps of:

heating a mixture comprising 0.1–10 weight % of a phytosphingosine powder in distilled water at 60–90° C. with stirring;

neutralizing, in pH, the mixture by adding lactic acid to solubilize the phytosphingosine with stirring whereby to form a neutralized solution; and adding a willow bark extract to prevent recrystallization of the neutralized solution.

2. The method as set forth in claim 1, wherein the phytosphingosine powder is present in the mixture in an amount of 0.5–6 weight %.

3. The method as set forth in claim 1, wherein the lactic acid is added at an amount of 0.2–4 g per g of the phytosphingosine.

4. The method as set forth in claim 1, wherein the willow bark extract contains about 10 weight % of salicylic acid and salicin.

5. The method as set forth in claim 1, wherein the willow bark extract is added at an amount of 0.2–10 weight %.

* * * * *